Figure 1:
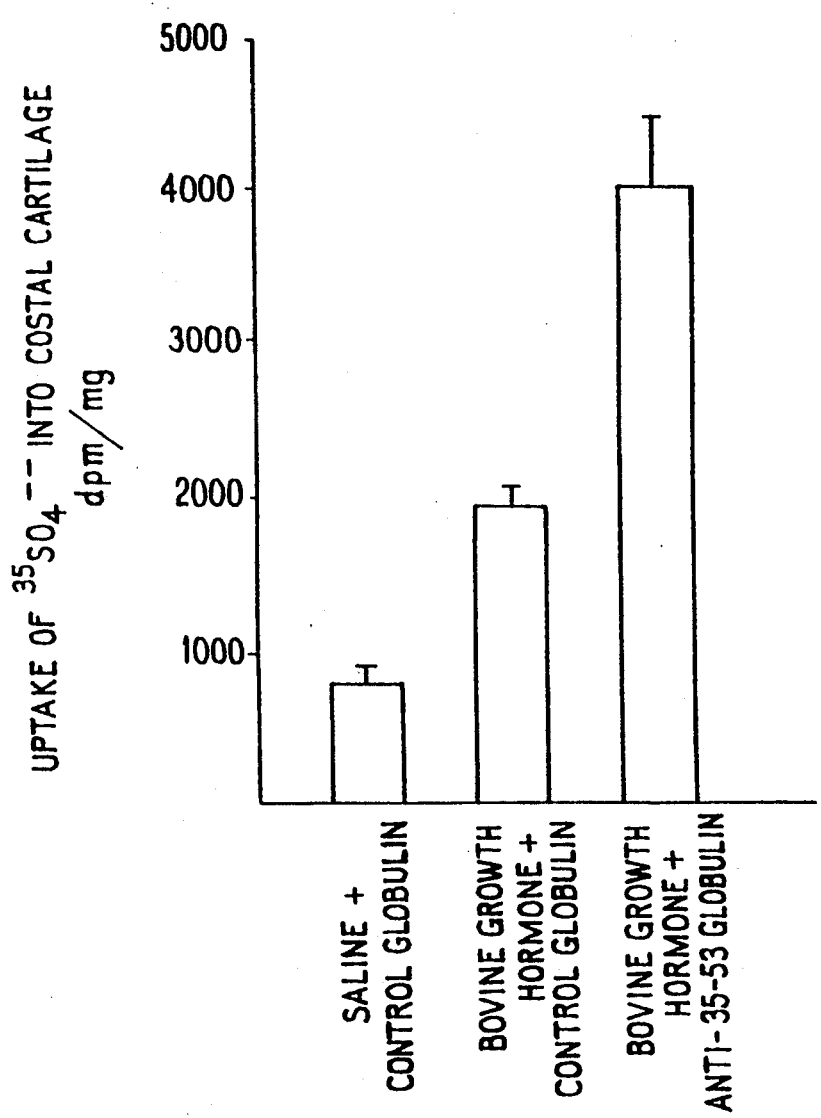

United States Patent [19]

James et al.

[11] Patent Number: 5,401,829
[45] Date of Patent: Mar. 28, 1995

[54] BIOLOGICALLY ACTIVE MOLECULES

[75] Inventors: Stephen James, Hertfordshire, England; Roger Aston, New South Wales, Australia; Robert Bomford, Kent, England

[73] Assignee: Coopers Animal Health Ltd., Hertfordshire, England

[21] Appl. No.: 813,110

[22] Filed: Dec. 23, 1991

Related U.S. Application Data

[62] Division of Ser. No. 282,217, Jan. 23, 1989.

[30] Foreign Application Priority Data

Mar. 27, 1987 [GB] United Kingdom ............... 8707398

[51] Int. Cl.$^6$ ............... C07K 7/06; C07K 7/08; A61K 39/395; A61K 39/00
[52] U.S. Cl. ............... 530/326; 530/327; 530/328; 530/300; 530/806; 424/185.1; 424/195.11
[58] Field of Search ............... 530/324, 326, 325, 327, 530/300; 514/2; 424/88, 85.8

[56] References Cited

PUBLICATIONS

Lewis et al, Bioch. Biophy. Res. Comm. 92, 1980. pp. 511-516.
Yudaen et al, Bioch Biophys. Res. Comm 110(3) 1983. pp. 866-872.
Shechter et al, PNAS 76(6), 1979. pp. 2720-2724.
Frigeri et al, Biochem. Biophys Res Comm. 91(3), 1979. pp. 778-782.
VandeLaan et al, J. Protein Chemistry 2(4), 1983. pp. 341-346.
Aston et al, Mol Immunol 24(2), 1987. pp. 143-150.
Aston et al, J. Endocr. 110, 1986. pp. 381-388.
Holder et al, J. Endocr. 107, 1985. pp. R9-R12.

*Primary Examiner*—Christine M. Nucker
*Assistant Examiner*—Chris Dubrule
*Attorney, Agent, or Firm*—Donald Brown; Peter F. Corless

[57] ABSTRACT

A peptide having primary structural homology to a continuous sequence of amino acid residues of growth hormone in the region spanning positions 35 to 53 or antigenically equivalent peptides thereto or salts thereof, may be used in an antigenic formulation to potentiate the effects of growth hormone in a vertebrate.

6 Claims, 9 Drawing Sheets

BIOLOGICALLY ACTIVE MOLECULES

This is a divisional of application Ser. No. 07/282,217, filed on Jan. 23, 1989.

The present invention relates to biologically active molecules, more particularly peptides.

Many polypeptide hormones are important medically or in animal husbandry, particularly growth hormones. Growth hormones are found in all vertebrates, the growth hormone (GH) of each species usually having a slightly different amino acid sequence from that of the GH of another species. Generally speaking, the molecule comprises a single linear sequence of about 191 amino acids. The amino acid sequence of human growth hormone (hGH) is described by Choh Hao Li in "Molecular and Cellular Biochemistry", 46, 31–41 ( 1982). Growth hormones are known to enhance growth (somatogenesis), to enhance milk production (lactogenesis) and to have an insulin-like hypoglycaemic effect.

It is known from EP-A-137 234 (Wellcome) that certain antibodies to growth hormone can potentiate the activity of the whole hormone, whereas previously it was generally thought that antibodies, at least in vivo, would antagonise the action of the hormone. Such potentiating antibodies may be produced in situ by vaccinating the host animal with a suitable fragment of growth hormone, so that a class of polyclonal antibodies of restricted specificity is created, which will potentiate the activity of the endogenous hormone. A large (7K) fragment is disclosed in this earlier document as being suitable for such a purpose.

It is also known, for example from WO84/04915 (Amgen), that peptides corresponding to portions of the GH molecule can have useful biological activity, in particular to generate hypoglycemic effects when administered contemporaneously with exogenous insulin. WO84/04915 does not teach one to administer such peptides in an antigenic formation, since the purpose of administration in WO84/04915 is not to raise antibodies against the peptide.

It has now been found that particular partial sequences of the GH molecule are especially suited to raising antibodies which will potentiate the activity of the hormone in a vertebrate. These peptides are substantially smaller than the 7K fragment referred to above, and hence can be synthesised more easily and cheaply.

The present invention provides a method for potentiating the effect of a pre-selected biologically active peptide, e.g. a hormone, in a vertebrate. The method uses small peptides containing pre- determined sequences of amino acid residues that have primary structural homology with fragments of the biologically active peptide and comprises treating the vertebrate with a predetermined amount of the small peptide to enhance the effect of the pre-selected biologically active peptide.

The present invention also provides small peptides containing amino acid sequences of a hormone of a vertebrate, which small peptides potentiate the activity of the hormone in the vertebrate. Typically, the peptides of the invention are about 25 amino acid residues or less, and more preferably less than 20 amino acid residues. The number of amino acid residues that have structural homology with the hormone which are contained in the small peptides of the invention are typically dependent upon the length of the small peptide and may vary from a sequence of a few amino acid residues to a sequence substantially comprising the entire small peptide. Typically, the sequence of amino acid residues having the structural homology is at least 5 amino acid residues in length and preferably at least about 8 to 10 amino acid residues in length.

As used herein the term "potentiate" means that the small peptide acts directly or indirectly to increase or enhance the activity of the hormone to which it has the structural homology.

Accordingly, one aspect of the present invention provides a peptide having primary structural homology to a (preferably continuous) sequence of amino acid residues of bovine growth hormone in the region spanning positions 35 to 53 thereof or antigenically equivalent peptides thereto or salts thereof.

The said region of bovine (and ovine) GH is: NH$_2$-Thr-Tyr-Ile-Pro-Glu-Gly-Gln-Arg-Tyr-Ser-Ile-Gln-Asn-Thr-Gln-Val-Ala-Phe-Cys-COOH.

By "primary structural homology" we mean: peptides which precisely duplicate this region; peptides which duplicate corresponding regions of growth hormone molecules from other species; and other peptides which have minor deletions or conservative substitutions of one or more amino acids such that the tertiary configuration of the peptide is substantially unchanged. The term "conservative substitution" is defined functionally above. Examples of substitutions which may be conservative in this context include those having substantially the same hydrophobicity, size, charge and/or aromaticity as the original amino acid residue. All such substitutions and modifications are generally well known to those skilled in the art of peptide chemistry. For example, candidate substitutions include: proline for glycine and vice versa: alanine or valine for glycine and vice versa; isoleucine for leucine and vice versa; tryptophan for tyrosine and vice versa; histidine for lycine and vice versa; serine for asparagine and vice versa; arginine for glutamate and vice versa; threonine for cysteine and vice versa; serine or alanine for threonine and vice versa; and glutamine for asparagine and vice versa.

The following are examples of regions of non-bovine GH's which correspond to the 35–53 region of the bovine growth hormone:

Human 35–53
NH$_2$-Tyr-Ile-Pro-Lys-Glu-Gln-Lys-Tyr-Ser-Phe-Leu-Gln-Asn-Pro-Gln-Thr-Ser-Leu-Cys-COOH.

Porcine and rat 35–53
Ala-Tyr-Ile-Pro-Glu-Gly-Gln-Arg-Tyr-Ser-Ile-Gln-Asn-Ala-Gln-Ala-Ala-Phe-Cys Arian (35–53)
Thr-Tyr-Ile-Pro-Glu-Asp-Gln-Arg-Tyr-Thr-Asn-Lys-Asn-Ser-Gln-Ala-Ala-Phe-Cys Salmon (or trout ) 31–49
Thr-Leu-Leu-Pro-Asp-Glu-Arg-Arg-Gln-Leu-Asn-Lys-Ile-Phe-Leu-Leu-Asp-Phe-Cys The term "antigenically equivalent" means that the peptide can be used, in a suitable formulation, to raise antibodies in a vertebrate, the antibodies acting to potentiate the action of growth hormone in that vertebrate. In particular, peptides which are slightly shorter or longer than the said regions or which overlap substantially with the said regions, for example 30–48 or 26–43, have been found to be antigenically equivalent. The terms "slightly longer", "slightly shorter" and "substantial overlap" denote peptides in which at least 45% (preferably 50%, 60%, 70%, 80%, 90% or 100%) of the equivalent peptide overlaps with at least 35% (preferably 40%, 50%, 60%, 70%, 80%, 90% or 100%)

of the said 35–53 regions. In particular, antigenically equivalent peptides which are shorter than the said fragments may be used, for example 35–43, or 35–48.

With specific although not exclusive relation to bovine GH, the following sequences are useful in the practice of the invention: 26–43 (Ala-Tyr), 35–43 (Thr-Tyr), 37–48 (Ile-Thr), 39–46 (Glu-Gln), 43–54 (Tyr-Phe) and 43–61 (Tyr-Pro).

It has been found that using a small peptide of the invention from a species other than the animal to which the peptide is being administered can be advantageous, for example, administering porcine 35–53 to sheep or cattle. Variations from the sequence of the animal's own GH may cause a greater immune response, whilst still yielding antibodies able to recognise the animal's own GH.

In addition, peptides in which one or more of the amino acid residues are chemically modified, before or after the peptide is synthesised, may be used providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats such as 35–53+35–53. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

A second aspect of the invention provides a pharmaceutical antigenic composition comprising one or more of any of the peptides of the first aspect of the invention, with means to provide carrier and adjuvant functions.

According to current immunological theories, a carrier function should be present in any immunogenic formulation is order to stimulate, or enhance stimulation of, the immune system. It is thought that carriers embody (or, together with the antigen, create) a helper T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed helper T-cell epitopes such as Thr-Ala-Ser-Gly-Val-Ala-Glu-Thr-Thr-Asn, betagalactosidase and the 163–171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-male imidomethyl)cyclo-hexane-1-carboxylate, the latter agent exploiting the —SH group on the C-terminal cysteine residue of the 35–53 region.

Suitable adjuvants are known to those in the vaccine art, for example Freund's complete or incomplete adjuvant, aluminium hydroxide, saponin, DEAE-dextran, muramyl dipeptide, mineral oils, neutral oils ( such as miglyol) vegetable oils (such as arachis oil), "Iscoms", liposomes, Pluronic polyols or the Ribi adjuvant system (see, for example, GB-A-2 189 141) . "Pluronic" is a Registered Trade Mark.

The peptide of the invention may be linked to other antigens to provide a dual effect. For example, the peptide may be linked to part or all of the somatostatin molecule to create, in addition to anti-GH antibodies, anti-somatostatin antibodies which would promote growth, or it may be linked to part or all of a sex hormone molecule to provide for simultaneous immunocastration, or to part or fall of the luteinising hormone releasing hormone (LHRH).

The peptides and adjuvants and/or carriers may be formulated in any suitable way which may be devised by the man skilled in the art using known or yet-to-be-discovered delivery vehicles and criteria. In particular, the formulations may be based on biodegradable polymers such as lactide glycolide copolymers, such as those described in EP-A-58481 (ICI).

A further aspect of the invention provides a method of treating a normal or abnormal vertebrate with a small peptide or antigenic composition as described above, in order, for example, to boost the growth of that vertebrate beyond normal levels or at an accelerated rate, to bring abnormally low levels of growth up to the norm, to boost milk yield or to boost or enhance other biological effects associated with GH. The proportion of lean meat to fat in an animal may also be enhanced by using such methods. The term "vertebrate" includes humans and non-humans.

The small peptides and antigenic compositions of the invention will usually be administered intravenously, sub-cutaneously or intra-muscularly although intra-nasal, transdermal, oral and rectal routes may be suitable for the some formulations of the invention. The formulation will normally be sterile and (for parenteral use ) non- pyrogenic and a unit dose will typically include 1 to 1000 ug of the small peptide of the invention, typically 10 to 500 ug, preferably about 50 ug or less. One or more repeat immunisations may be advantageous, as is known in the art of immunology. The formulations may generally be prepared and/or administered by a physician or veterinary surgeon according to his skill and expertise.

A further aspect of the invention provides a process for preparing one of the peptides mentioned above, by known methods of peptide synthesis or by appropriate cleavage of the native GH molecule. Peptide synthesis may be achieved according to the general method of Stewart et al, described in "Solid Phase Peptide Synthesis" (W H Freeman, San Francisco, 1969) or by the methods described by Marglin and Merrifield in Annual Reviews of Biochemistry 39, 841–866 at 862 (1970), and subsequent articles. Established methods of peptide synthesis by solid phase and similar techniques are usually not suitable for large scale production (although they may become so in the future ) and thus commercial production of the peptides would normally be by cultivation of a suitable organism transformed with a polynucleotide sequence encoding the desired peptide. Thus, further aspects of the invention include such polynucleotides, transformation and expression vectors carrying such polynucleotides, organisms transformed therewith and processes for cultivating such organisms.

A further aspect of the invention includes non-human vertebrates whose characteristics have been altered by methods in accordance with the invention.

Figure 2:
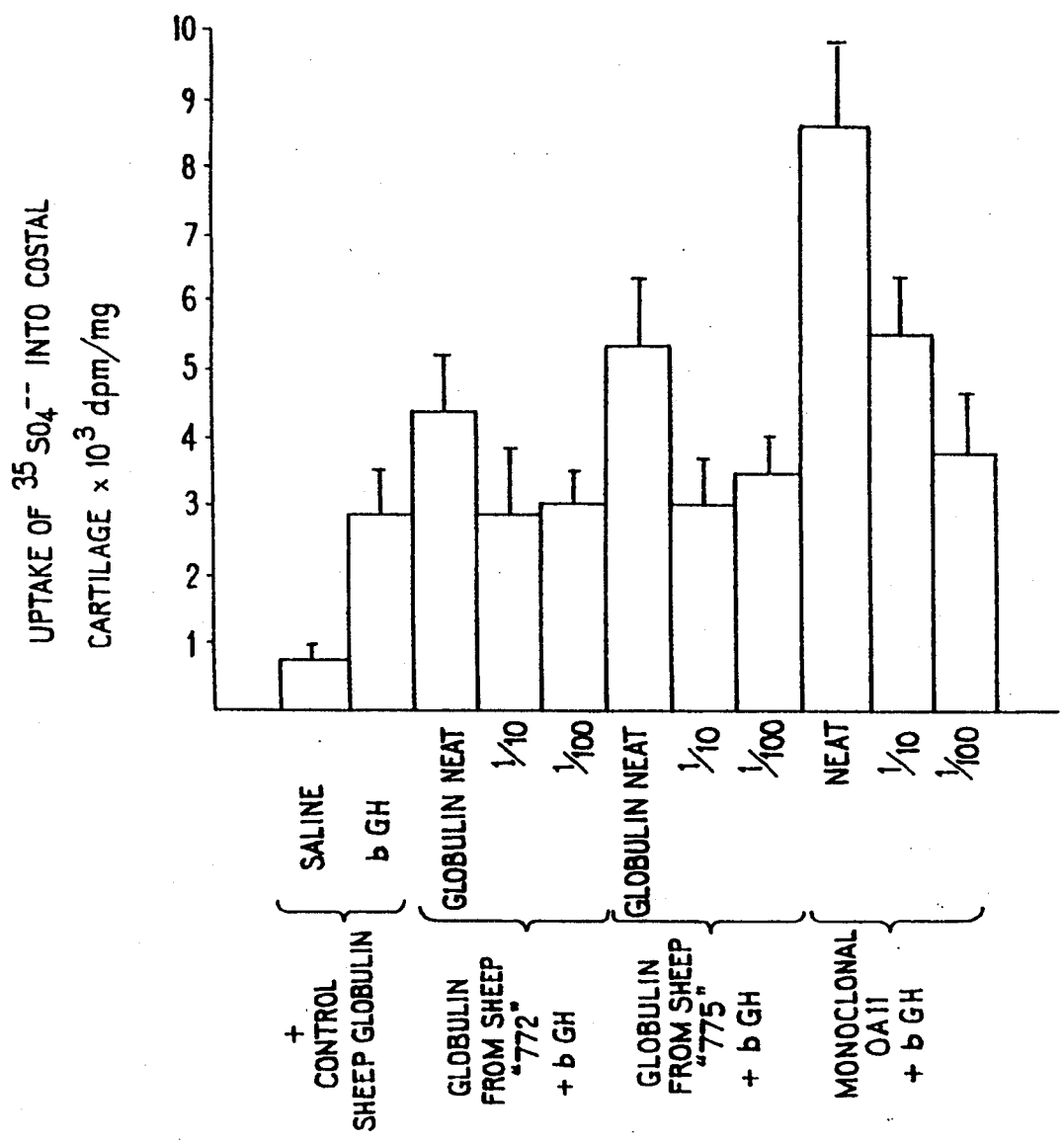
Figure 3:
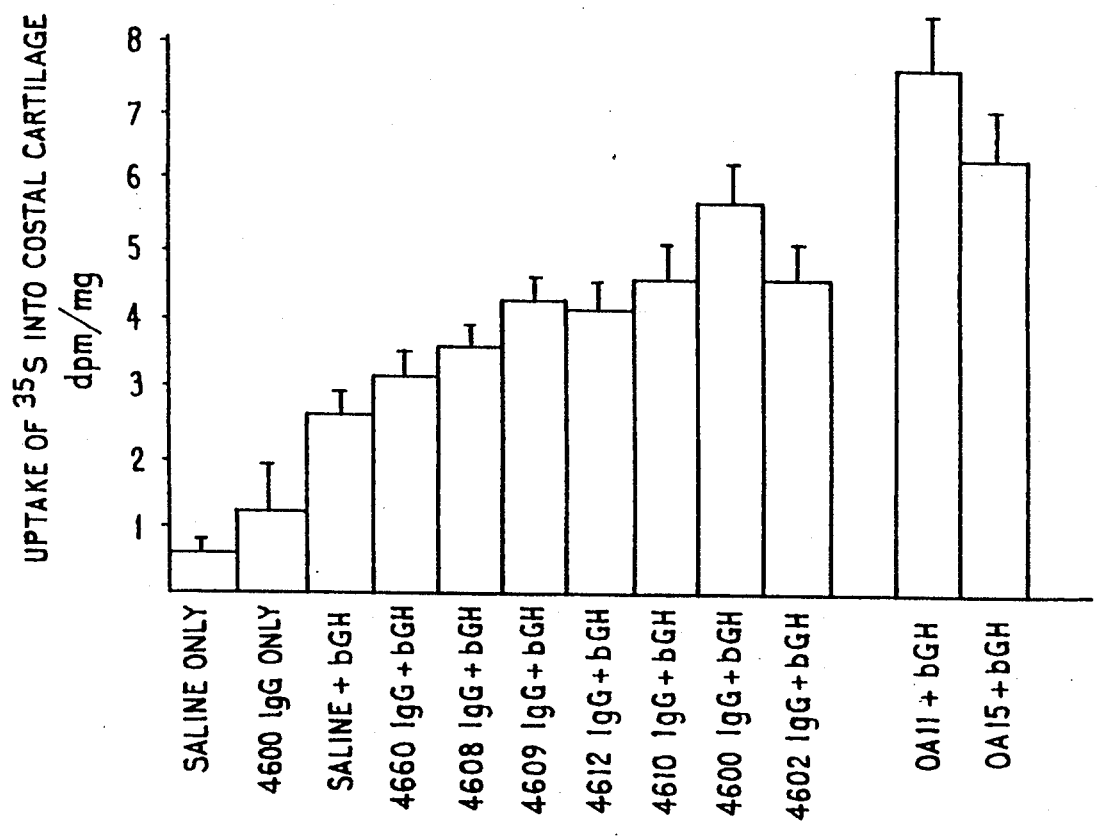
Figure 4:
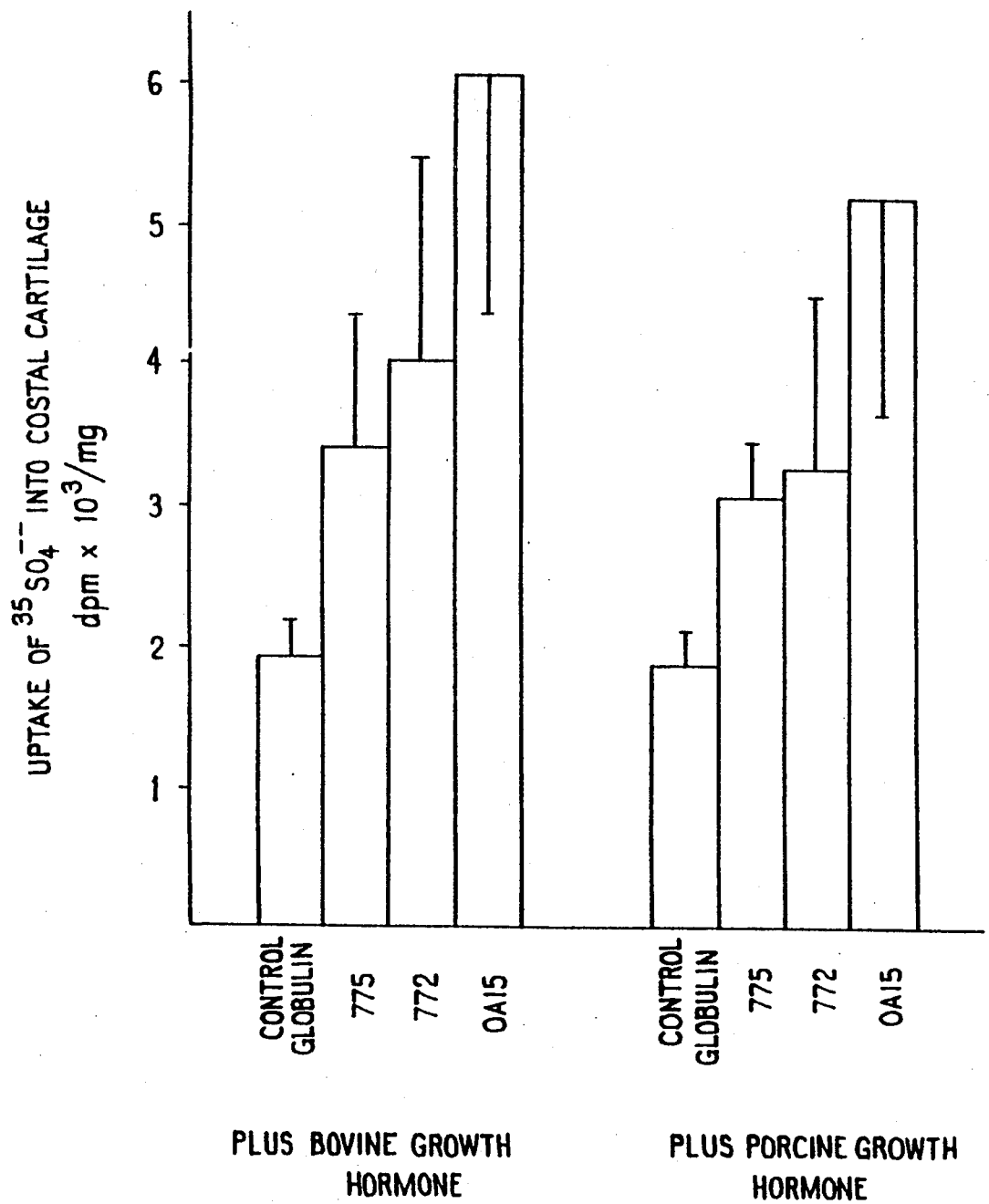
Figure 5:
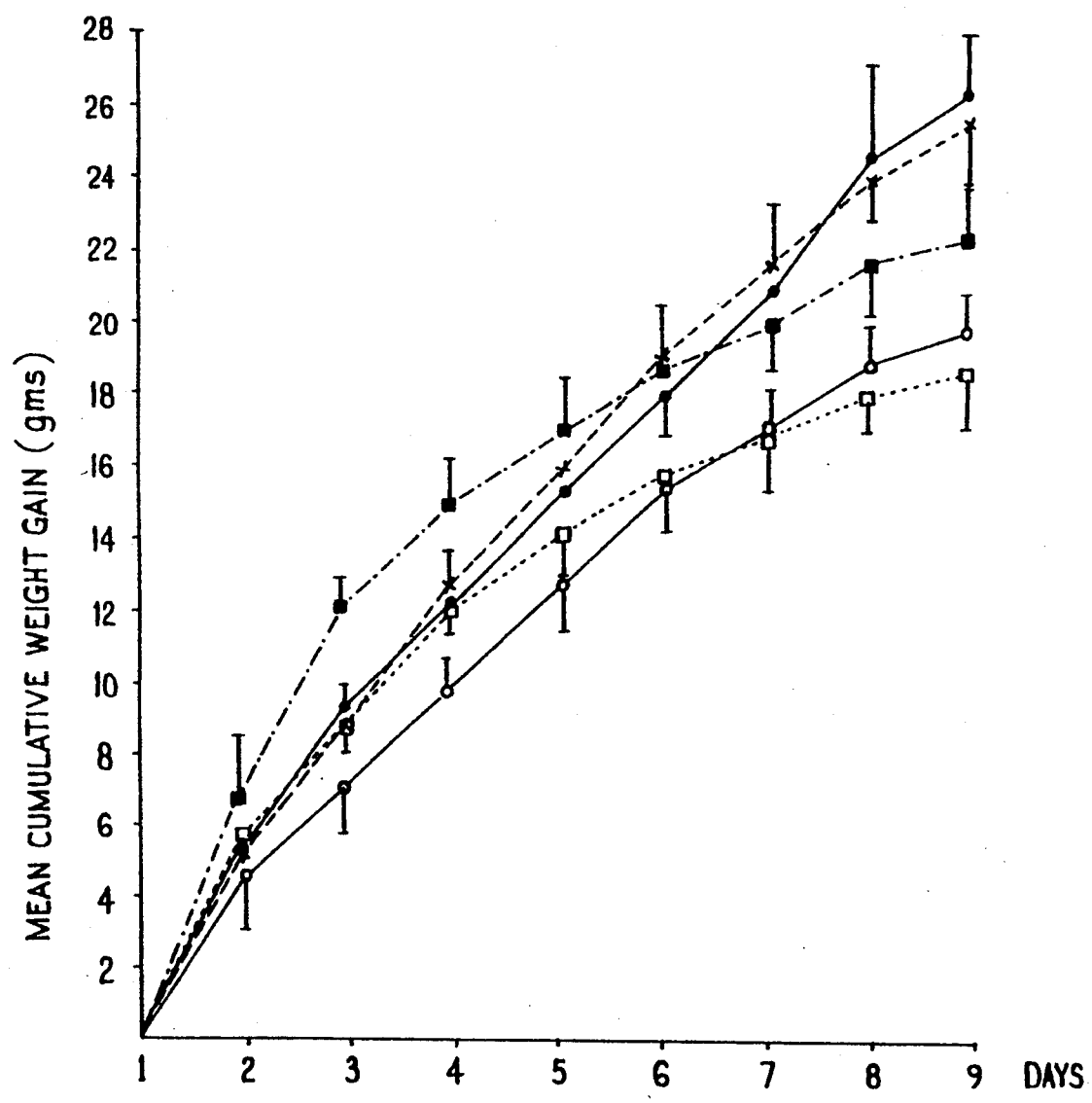

Examples in accordance with the invention will now be described, with reference to the accompanying drawings, in which:

FIG. 1 shows the results of a preliminary dwarf mouse experiment. Bars represent 1 s.d. with 6 animals per treatment;

FIG. 2 shows the results of a second dwarf mouse experiment, in which activity of IgG (globulin) from two sheep 772 (35–53 only+FCA) and 775 (35–53 conjugated to KLH+FCA) was compared with OA11 at different globulin concentrations. 772 neat=10.5mg protein/ml; 775=9.6 mg protein/mi. OA11—5mg protein/mi. Bars=1 s.d.; n=6;

FIG. 3 shows the results of a third dwarf mouse experiment, showing the activity of globulins from different sheep all having been treated with 35–53 X-linked+FCA (4600, 4609, 4602, 4612, 4610) or negative control immunisation (4660, 4608). Bars—1 s.d., n=6;

FIG. 4 shows how antisera raised to b35–53 in different ways can, in some cases, bind to bovine growth hormone and the porcine molecule. Affinity for the latter is reduced by approximately 10×. The results of a dwarf mouse experiment are shown. Bars=1 s.d., n=6;

FIG. 5 shows the results of a hypophysectomised rat experiment, carried out as described below, showing the weight gain of groups (n=6) of rats across the 9 day period. Bars represent 1 s.d. All treatments received hormone.

Figure 6:
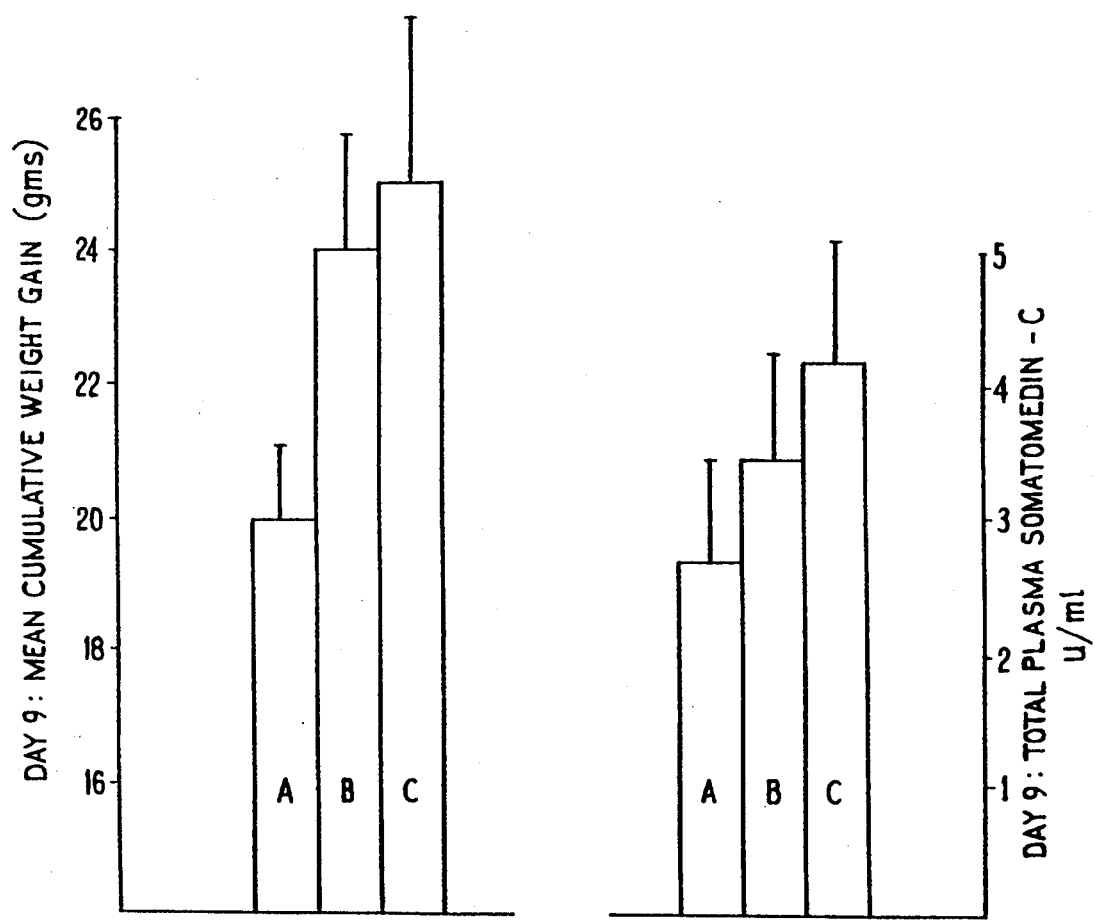
Figure 7:
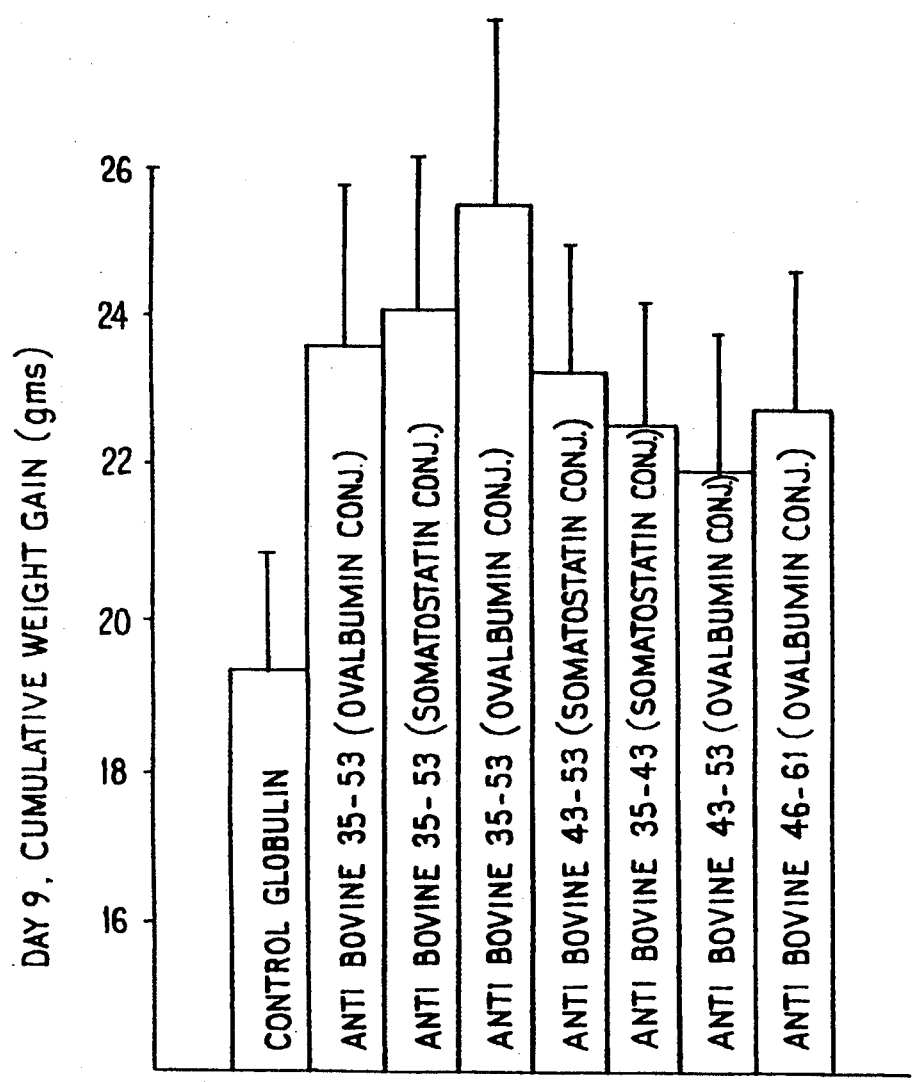
Figure 8:
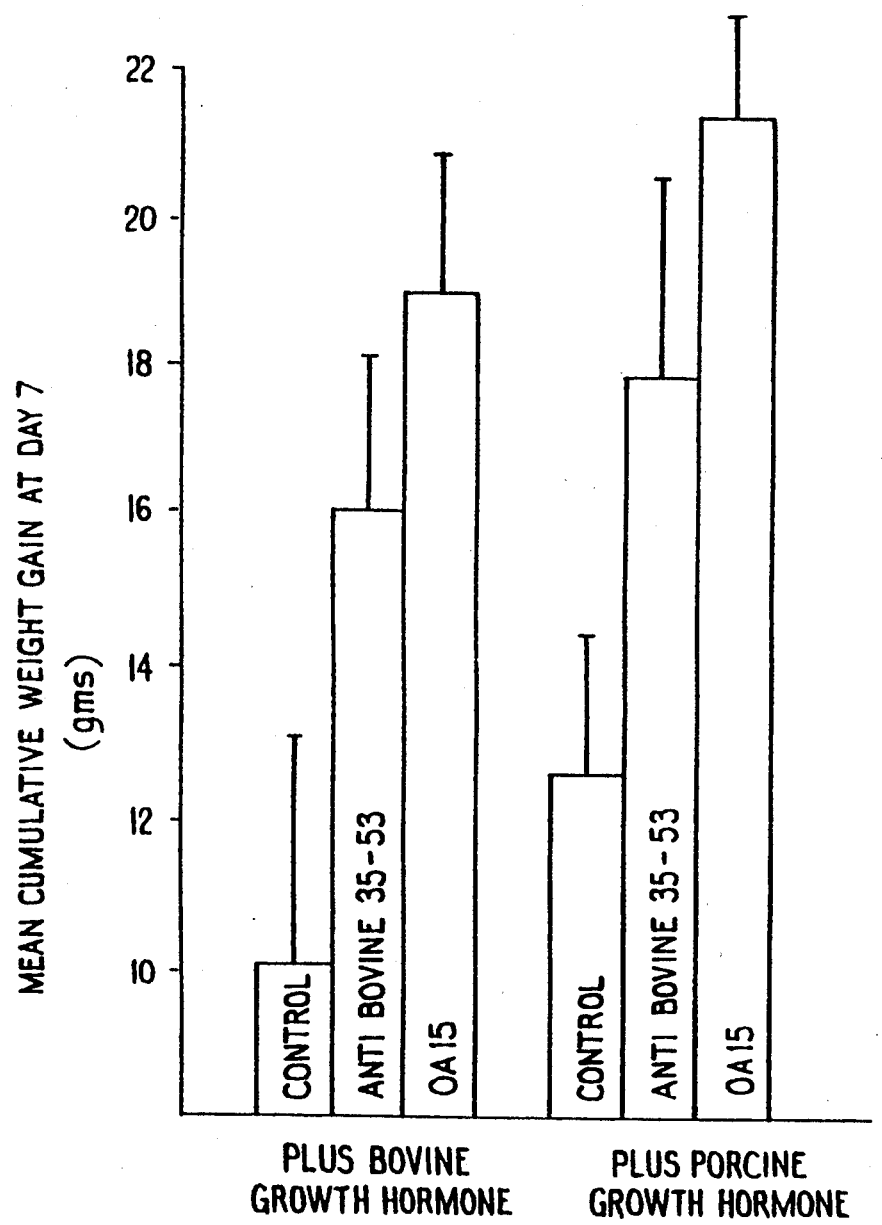
Figure 9:
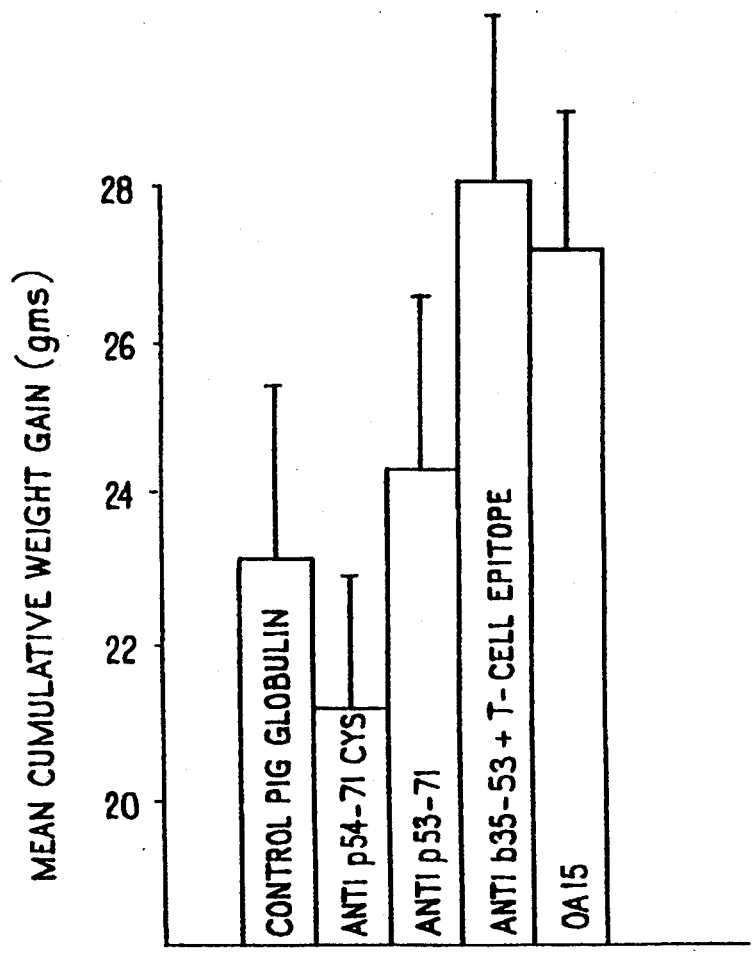

- ● anti-bovine 35–53 anti-sera pooled from 4 immunised sheep, positive for bovine growth hormone binding (RIA).
- x anti-sera as above from one of the four sheep.
- o negative control anti-sera.
- ■ monoclonal antibody (treated as antisera) OA15.
- □ monoclonal antibody OA17 (See Aston et al, 1986);

FIG. 6 shows the result of a further hypophysectomised rat experiment.
A: control sheep immunoglobulin.
B: anti-35–53 antisera, sheep 1064, 5mg/ml.
C: anti-35–53 antisera, sheep 1064, 15 mg/ml. neat.
Bars represent 1 s.d.; n=6;

FIG. 7 shows the results of a further hypophysectomised rat experiment, namely a comparison of antipeptide antibodies conjugated to either ovalbumin or somatostatin.
Bars represent 1 s.d., n=6.
Each of these globulin preparations was complexed with bovine growth hormone prior to administration to the rats;

FIG. 8 shows the results of a further hypophysectomised rat experiment, illustrating how anti-bovine 35–53 could also enhance porcine growth hormone; rats were dosed at only 15 ug per day but with the usual level of anti-globulin. Bars represent 1 s.d., n=6;

FIG. 9 shows the results of another hypophysectomised rat experiment, in which rats were treated with anti-peptide antibodies raised to a variety of peptides related to either bovine or porcine molecules. All were complexed with porcine growth hormone prior to administration to rats. Bars represent 1 s.d., n=6.

METHODS

Preparation of peptides

All peptides were synthesised by the Fmoc-polyamide mode of solid-phase peptide synthesis.

Temporary Nα-amino group protection is afforded by the 9-fluorenylmethyloxycarbonyl (Fmoc) group. Repetitive cleavage of this highly base-labile protecting group is effected using 20% piperidine in N,N-dimethylformamide.

Side-chain functionalities are protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenhydryl group for protection of the side chain amido functionalities.

The solid-phase support is based on a polydimethylacrylamide polymere constituted from the three monomers dimethylacrylamide (backbone-monomer), bisacryloylethylene diamine (cross linker) and acryloylsarcosine methyl ester (functionalising agent).

The peptide-to-resin clearable linked agent used is the acid-labile 4-hydroxymethyl-phenoxyacetic acid derivative.

All amino acid derivatives are added as their preformed symmetrical anhydride derivatives with the exception of asparagine and glutamine that are added using a reversed N,N-=dicyclohexylcarboniimide/1-hydroxybenzotriazole mediated coupling procedure.

All coupling and deprotection reactions are monitored using ninhydrin, trinitrobenzene sulphonic acid or isotin test procedures.

Upon completion of synthesis, peptides are cleaved from the resin Support with concomitant removal of side-chain protecting groups by treatment with 95% trifluoroacetic acid containing a 5% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers.

Purification may be effected by any one, or a combination of, techniques such as size exclusion chromatography, ion-exchange chromatography and (principally) reverse-phase high performance liquid chromatography.

Analysis of peptides is carried out using thin layer chromatography, reverse-phase high performance liquid chromatography, amino-acid analysis after acid hydrolysis and by fast atom bombardment (FAB) mass spectrometric analysis, as is well known to those skilled in the art.

I. SHEEP EXPERIMENTS: PRELIMINARY

Methods: 1: Preparation of immunogenic composition
Cross-linking to keyhole limpet haemocyanin using glutaraldehyde:

10 mg of peptide (ovine/bovine sequence 35–53 ) was dissolved in 500 ul dimethyl formamide, and mixed with 10 mg of keyhole limpet haemocyanin in 400 ul of 0.05M phosphate buffer pH 7.8. 1 ml of 0.02M glutaraldehyde solution in 0.05M phosphate buffer pH 7.8 was added dropwise over one hour whilst stirring at room temperature. The mixture was allowed to stir at room temperature for a further three hours and then dialysed versus phosphate buffered saline pH 7.2.

Half the preparation was mixed with a double volume of Freund's complete adjuvant and injected into two sheep at multiple subcutaneous sites. 28 days later, the second half of the preparation was similarly emulsified and injected in Freund's incomplete adjuvant. The sheep were bled at weekly intervals during immunization, the optimum antibody response being obtained around 14 days after the second immunization.

2. Radioimmunoassay of sheep sera

Antibody production by sheep following immunization with GH peptide fragment 35–53 was determined by liquid phase direct binding assay with $125^{I\text{-}bGH}$ essentially as described previously (Aston, et al, 1985).

3. Growth assay

Growth enhancing peptide antisera (anti-35–53) were assessed for activity, after preparation of γ-globulins from the sera, in the dwarf mouse growth model as described previously. (Aston, et al, 1986;1987).

Results

Sera from sheep immunized with peptides derived from bovine/ovine GH were assessed for their binding to $^{125}$I-bGH and their effects on the bioactivity of bGH in vivo. Dwarf mice receiving bGH in complex with anti-35–53 antiserum grew significantly better than those treated with bGH and control sheep globulin.

The results are shown in FIG. 1.

II—SHEEP EXPERIMENTS: INVESTIGATORY

Methods 1. Conjugation to ovalbumin or Keyhole Limpet Haemocyanin (KLH)

1.4 mg of peptide (e.g., bovine 35–53) was dissolved in 140 ul of dimethyl formamide. 70 ul of 10 mg/ml ovalbumin or KLH in Dulhecco's phosphate buffered saline (PBS) was added and thoroughly mixed. 200 ul of freshly prepared 0.04M glutaraldehyde was added slowly, with stirring, over a period of 10 minutes then left at room temperature for a further 60 minutes. 0.7 ml of PBS was added and followed by a further 100 ul 0.04M glutaraldehyde as above. This was left for 60 minutes at room temperature before being dialysed overnight at +4° C. against PBS.

2. Cross-linking 1.4 mg of peptide was dissolved in 140 ul dimethyl formamide and 170 ul of 0.04M glutaraldehyde was added as above. Otherwise as above. If no cross-linking nor conjugation was required the peptide was dissolved in dimethyl formamide, dispersed in PBS but not dialysed.

3. Negative Controls

Negative control parallels for the above were produced by using no peptide with ovalbumin (or KLH) or using poly-lysine (molecular weight 1000–2000 Da) and cross-linking.

4. Adjuvants & Administration—'Freunds'

After dialysis, the volumes of the above preparations were made up to 4.5 mls with PBS and 'water-in-oil' emulsions prepared using two volumes of Freund's Complete Adjuvant (FCA) (Difco or Sigma). This was achieved by sonication in the cold or using a Potter-Elvehjen homogeniser. Emulsions were tested by dispersion (or absence) on a water surface. The injections were subcutaneously administered at two sites (one on each flank) into Cheviot sheep (9–12 months old, castrate males, 30–35 kg). 1 ml was administered at each site. A second, similar immunisation was completed using freshly prepared peptide conjugated in the same way but emulsified into Freund's Incomplete Adjuvant (FIA) (Difco or Sigma). Any subsequent immunisations were similar, but at 28 day intervals.

5. Adjuvant & Administration—Others

DEAE-dextran (fully hydrated overnight in double-distilled water) (Pharmacia), Saponin (Sigma) and aluminium hydrogel were used alone and in combinations. After dialysis, additions were made of 3.1 ml PBS plus 7 ml 5% DEAE-dextran (Dd) plus 2.8 ml of 5 mg/ml Saponin; or 5.9 ml PBS plus 7 ml 5% Dd; or 10.1 ml PBS plus 2.8 ml 5 mg/ml saponin. Aluminium ("AlOH") was used at 1.0 mg/ml final concentration where appropriate.

No emulsification was required but care was taken to maintain the constituent in homogenous suspension. 1 ml was administered into sheep as described above. Immunisations were carried out at the same intervals.

6. Blood Samples 10 ml blood samples were taken by jugular venepuncture, from the sheep under test, just prior to any administration and at 3 × weekly intervals thereafter. After allowing the clot to form at room temperature (approximately 5 hours) the serum was removed after centrifugation for immediate antibody-detecting radioimmunoassay. Larger samples of sera were collected in the same way from approximately 150 mls of blood, were frozen at −20° C. for subsequent fractionation and use in growth assays.

7. Radioimmunoassay

The detection of antibodies to peptides which would also bind to bovine growth hormone was determined by liquid phase direct binding as described previously (Aston et al, 1985; Chard, 1987).

Results

Table 1 summarises the results from the sheep experiment's and indicates the superiority of FCA with most conjugates (or peptide alone) using peptide 35–53. Small changes as in porcine 35–53 introduced into sheep further improved the response rate (as well as the actual titre—not shown). Peptides around, but including, and within the 35–53 sequence produced at least moderate responses.

TABLE 1

Radioimmunoassay to detect antibodies in sheep sera which were capable of binding to intact bovine growth hormone in liquid phase.

| Treatment | | % Responders at 56 days with titre of 1/1000 or more (n = 5). |
|---|---|---|
| Bovine 35-53 variations: | | |
| Conjugate | Adjuvant | |
| KLH | FCA | 60 |
| KLH | AlOH | none |
| KLH | Saponin | 20 |
| KLH | Dd | 20 |
| KLH | Dd + AlOH | 20 |
| Ovalbumin | *FCA (sonicated) | 20 |
| Ovalbumin | *FCA | 80 |
| Ovalbumin | AlOH | 20 |
| Ovalbumin | Saponin | 60 |
| Ovalbumin | Dd | none |
| Ovalbumin | Dd + AlOH | 80 |
| Crosslinked | FCA | 80 |
| Crosslinked | Saponin | 20 |
| Crosslinked | Dd + Saponin | 80 |
| Crosslinked | Dd alone | 20 |
| None | FCA | 40 |
| | AlOH | 20 |
| | Saponin | 20 |
| | Dd | 20 |
| | Dd + AlOH | 20 |

TABLE 1-continued

Radioimmunoassay to detect antibodies in sheep sera which were capable of binding to intact bovine growth hormone in liquid phase.

| Treatment | % Responders at 56 days with titre of 1/1000 or more (n = 5). |
|---|---|
| Other peptides - all above bovine (unless indicated) conjugated to ovalbumin and administered in FCA. | |
| 46-61 Cys | 60 |
| 43-53 | 20 |
| 35-43 Cys | 20 |
| Porcine 35-53 | 100 |

*Unless indicated otherwise, emulsions were prepared by shearing.

III—IMMUNOSTIMULATORY EFFECTS

Method

An experiment was conducted to demonstrate that the 35-53 (or its analogues and related sequences) could be linked to another peptide or molecule of immunological interest and the response to both peptides be improved.

In this context, and especially relevant to the role of immunoneutralisation in animals, somatostatin was selected for illustrative purposes and for the difficulty in raising effective immunoneutralising antibodies (see Spencer, 1986).

Using (1-14) somatostatin (Sigma) the conjugation was completed as described above (II-I) except that somatostatin was added at only 4 mg/ml and that no dialysis was carried out in any of the treatments. All other conjugates were prepared as described above (II-I).

Radioimmunoassays for growth hormone binding antibodies were as above (II-7) for somatostatin as described by Spencer et al, (1983) using $^{125}$I-labelled Tyr-somatostatin.

Results

The data summarised by Table 2 illustrate the customary difficulty in raising good antibody titres to somatostatin and how the cross-linking to bovine 35-53 (not merely internal cross-linking) striking overcomes this tolerance to self.

TABLE 2

Radioimmunoassays for antibodies to intact bovine growth hormone and/or to somatostatin after an immunisation procedure utilising 35-53-somatostatin conjugation.

| Treatment | % antibody producers (n = 5) recognising | |
|---|---|---|
| | bGH | Somatostatin |
| crosslinked 35-53: | | |
| FCA | 80 | none |
| FIA | none | none |
| Dd + Saponin | 80 | none |
| crosslinked somatostatin: | | |
| FCA | none | 40 |
| FIA | none | none |
| Dd + Saponin | none | none |
| 35-53 plus somatostatin: | | |
| FCA | 80 | 80 |
| FIA | 40 | 60 |
| Dd + Saponin | 80 | 40 |
| Linked to somatostatin— (c.f. Table 1) | | |
| 35-43 Cys | 60 | 40 |
| 43-53 | 40 | 40 |

IV—PIG EXPERIMENT

Methods

1. General

Sequence 35-53 plus the T-cell epitope described earlier, i.e. Thr-Ala-Ser-Gly-Val-Ala-Glu-Thr-Thr-ASN, was introduced into pigs after dissolving in dimethyl formamide, dispersing in PBS (see II-2) and emulsifying in FIA. No conjugation or cross-linking was used in this sequence.

The peptide so prepared was administered subcutaneously at 4 sites in the neck region of large White piglets (5 weeks of age; approximately 9 kg body weight) so as to give 500 ug peptide per pig. A second immunisation using a similar preparation was given 28 days later. On this occasion all were delivered in FIA. Blood samples were collected just prior to this immunisation and weekly thereafter, by vacuum-assisted venepuncture (Corvac, Sarstedt, U.K.) of the pulmonary vein. The sera were tested for antibody recognition of porcine growth hormone using an Enzyme Linked Immunosorbent Assay (ELISA) based on Voller, 1979, which was subsequently cross-linked by competition, in a similar assay, with aqueous hormone.

2. ELISA 96-well plates treated for immunoassy consistency (Nunc, Immuno-quality, High-binding capacity) were coated using 50 ug hormone/ml at 5 ug.well (100 ul) in sodium carbonate/bicarbonate buffer 0.05M pH9.5 and allowed to stand overnight at +4° C. The hormone solution was carefully removed and the wells washed once with PBS. A solution of 3% haemoglobin was added to 'block' the wells and left overnight at +4° C. This was removed and the wells washed three times with PBS to 0.05% Tween. All plates were allowed to dry slowly at room temperature and stored at −20° C. individually wrapped in cling-film. Sera under test were added to each of the wells at 1/50th and subsequent log$_{10}$ dilutions (100 ul) and left for 2 hours, at room temperature. This was removed and the wells washed three times in PBS, and replaced by 100 ul rabbit anti-pig IgG alkaline phosphate conjugate (Sigma) at 10$^{-3}$ dilution. This was removed and washed as before. 100 ul of p-nitrophenyl phosphate at 1.0 mg/ml was added and the absorbance of the wells read using Titertek Multiscan Plus 2 with 405 nm filter.

Results

Table 3 shows that the presence of antibodies which recognised coated porcine growth hormone (and this would compete with aqueous hormone) could be detected in a number of pigs.

TABLE 3

Anti-pGH antibodies in peptide immunised pigs at 42 days, as measured by the ELISA technique.

| Peptide Treatment | % Positive animals (n = 6) | |
|---|---|---|
| | 1/50* | 1/500* |
| 35-53 T-cell epitope | 100 | 100 |

*antisera dilution.

V—BIOLOGICAL ASSAYS OF GH ACTIVITY

Methods

1. Immunoglobulin Preparations

Sera from larger blood samples taken from particular animals (indicated by the immunoassays) were fractionated by sodium sulphate precipitation (Johnstone & Thorpe, 1982) to isolate principally the gamma-globulins (IgG) which were extensively dialysed against PBS before being re-frozen at −20° C. Prior to use in animal experiments the purified IgG fractions were re-titrated to monitor the effects of precipitation, if any.

2. Dwarf Mouse

This uses the incorporation of $^{35}SO_4^-$ into the rib cartilage of dwarf (pituitary deficient) mice and has been described elsewhere (Aston et al, 1986).

3. Hypophysectomised Rat

These animals are rendered pituitary (hypophysis) deficient by surgical removal. The assay monitors the overall effect of the hormone on body weight of the rat as well as the circulating levels of Somatomedin-C.

The surgery on male, Wistar rats was completed by Charles River U.K. Limited (Margate, kent, U.K.) and delivered 14 days later at a weight range of 125–145 g. They were weighed and observed for a further 7–10 days, to ensure stable body weight and physical features (for example non-appearance of testicles) consistent with good health and complete surgery. Satisfactory animals were randomly allocated to provide six animals per treatment. These were injected daily with 0.5 ml PBS containing approximately 1 mg sheep IgG from the immunisation treatment under study (including negative controls), to which had been added 50 ug (exceptionally 10 ug—see results) bovine or porcine growth hormone as appropriate. Before administration the hormone and IgG were mixed and allowed to stand at room temperature for 60 minutes. Injections were subcutaneous and intrascapular. Animals were weighed and injected daily for 8 days, at the same time of day on each occasion. On the ninth day the animals were weighed, terminally anaesthetised and a blood sample taken from the aortic bifurcation. EDTA-plasma was frozen at $-20°$ C. for subsequent estimation of relative total Somatomedin-C levels using materials supplied by Nichols Institute (San Juan Capistrano, Calif. 92675, USA).

Results

1. Dwarf Mouse Model

From the data summarised in FIGS. 2, 3 and 4 it can be seen how dwarf mice receiving growth hormone in complex with sheep anti-bovine (b)35–53 antisera incorporated significantly greater amounts of $^{35}S$ (from $Na_2{}^{35}SO_4$) into their costal cartilage than those treated with bGH and control sheep globulin. This occurs from variety of immunisation procedures and is related to antisera dilution prior to complexing (FIG. 2). This phenomenon can also be seen when an antiserum raised to bovine 35–53, which also recognises intact porcine growth hormone (albeit much more weakly than it recognises the homologous hormone), is complexed with it, when an enhanced $^{35}S$ incorporation into costal cartilage will be produced.

2. Hypophysectomised Rat Model

Using a growth-related model it can be seen (FIGS. 5–9) that a variety of anti-peptide sera will enhance the activity of bovine and porcine growth hormones when administered to these surgically modified rats.

In this system antisera to peptides related to the 35–53 region are active in enhancing the response to growth hormone (FIG. 7). This phenomenon will cross species barriers as shown (FIG. 7) provided that the antisera will bind to the target hormone in question. In certain cases if the binding capacity or affinity is limited it may be necessary to adjust the globulin:hormone ratio to maximise the proportion of hormone-antibody complexes, as shown in FIG. 8.

VI CONJUGATE ANTIBODIES (SOMATOSTATIN)

Method

Using the in vitro method described previously (Hart et al, 1984) the activity of the anti-somatostatin antisera upon the release of the growth hormone from ovine pituitary cells (in primary culture) was measured. Because the growth-hormone binding properties of the antibodies would interfere with the assay these were removed by passing down an affinity column to which bovine growth hormone had been attached. An activated Sepharose-CNBr column was prepared in the manner described by the manufacturer (Pharmacia, Milton Keynes, Bucks, U.K.).

Somatostatin-14 (Sigma) was added to wells in 10 ul of immune (anti-somatostatin activity by RIA) or nonimmune (anti-35–53 only) sheep sera across the range $5-250 \times 10^{-11}$ mol/L and the inhibitory activity of this peptide upon the levels of growth hormone release into the media was assessed.

Results

Table 4 clearly shows how the inhibitory activity of somatostatin, added in an antiserum containing somatostatin antibodies is markedly reduced. Thus, it is important to note that the antiserum raised against the bovine 35–53+somatostatin conjugate appears to contain two populations of antibodies—one which binds to intact bovine growth hormone and enhances its activity and another which binds to intact somatostatin-14 and neutralises it.

TABLE 4

Effect of somatostatin upon ovine pituitary cells grown in primary culture as described Hart et al, 1984

| Somatostatin level | Mean % Inhibition of GH release. | |
|---|---|---|
| | anti-35-53 only antisera | anti-somatostatin antisera |
| 5 | 5 | 5 |
| 25 | 10 | 5 |
| 125 | 70 | 20 |
| 250 | 90 | 70 |

References

1. Aston, R., Cooper, L., Holder, A. T., Ivanyi J. and Preece, M. A. (1985). Molecular Immunol. 22 271–275.
2. Aston, R., Holder, A. T., Preece, M. A., and Ivanyi, J. (1986). J. Endocrinol. 110 381–388.
3. Aston, R., Holder, A. T., Ivanyi, J. and Bornford, R. (1987). Molec. Immunol. 24 143–150.
4. Chard, T. (1987). An Introduction to Radioimmunoassay and Related Techniques. 3rd Edition. Elsevier, Amsterdam.
5. Hart, I. C., James, S., Perry, B. N., and Simmonds, A. D., (1984). J. Endocrinoi. 103 173–178.
6. Johnstone, A., and Thorpe, R. (1982) Immunochemistry in Practice, Blackwells, London.
7. Spencer, G. S. G. (1986). Control and Manipulation of Animal Growth. Pp 179–293, Butterworths, London.
8. Spencer, G. S. G., Garssen, G. J., and Hart, I. C., (1983). Livestock Production Science 10 25–37.
9. Voller, A., Bidwell, D. E. and Bartlett, A. (1979). The Enzyme Linked Immunosorbent Assay, Dynatech Europe, Guernsey.

We claim:

1. A pharmaceutical antigenic formulation comprising:

a peptide selected from the group consisting of: TYIPEGQRYSIQNTQVAFC

TYIPEGQRY
YSIQNTQVAFC
and
QNTQVAFCFSETIPAP,
and means to provide adjuvant and carrier functions.

2. A formulation according to claim 1 wherein the peptide is linked to a carrier.

3. A formulation according to claim 2 wherein the peptide is conjugated to (a) itself, (b) another peptide as defined in claim 1, (c) a T-cell epitope or (d) part or all of a somatostatin molecule.

4. A formulation according to claim 1 wherein the peptide is mixed with an adjuvant.

5. A formulation according to claim 4 wherein the peptide is linked to a carrier.

6. A formulation according to claim 4 wherein the peptide is not linked to a carrier.

* * * * *